United States Patent [19]

Drinkard

[11] 4,329,150

[45] May 11, 1982

[54] METHOD AND APPARATUS FOR CONTROL AND OPTIMIZATION OF PYROLYSIS FURNACE WITH MULTIPLE PARALLEL PASSES

[75] Inventor: B. M. Drinkard, Beaumont, Tex.

[73] Assignee: Mobil Oil Corporation, New York, N.Y.

[21] Appl. No.: 215,480

[22] Filed: Dec. 11, 1980

[51] Int. Cl.³ .................... G01N 25/22; G01N 31/12; G01N 33/22

[52] U.S. Cl. ............. 23/230 A; 23/230 PC; 364/500; 422/62; 422/78

[58] Field of Search .............. 23/230 PC, 230 A; 422/78, 62; 364/497, 500

[56] References Cited

U.S. PATENT DOCUMENTS 4,187,542 2/1980 Ball et al. .................. 23/230 A
4,241,230 12/1980 Drinkard .................... 422/62
4,249,908 2/1981 Funk ......................... 422/62
4,251,224 2/1981 Cowley et al. ............... 422/62
4,262,791 4/1981 Lynch et al. .............. 422/62 X Primary Examiner—Ronald Serwin
Attorney, Agent, or Firm—Charles A. Huggett; Michael G. Gilman; Edward J. Trojnar

[57] ABSTRACT

An improved method and apparatus for control of a multi-pass pyrolysis furnace, e.g. for the pyrolysis of hydrocarbon feed to produce an effluent with a high ethylene content is disclosed. The method which is suitable for computer control involves the analysis of the effluent from each pass and controlling pyrolysis conditions in each pass in response to the analysis of the output from that pass. Improved optimization is possible over methods which depend on average analysis from several passes because of the wide variations which occur in cracking conditions in several passes.

10 Claims, 2 Drawing Figures

METHOD AND APPARATUS FOR CONTROL AND OPTIMIZATION OF PYROLYSIS FURNACE WITH MULTIPLE PARALLEL PASSES

BRIEF SUMMARY OF THE INVENTION

This invention relates to the method and apparatus for the control and optimization of a pyrolysis furnace having multiple parallel passes. Optimization is achieved by analyzing furnace output at each of the several multiple parallel passes and controlling furnace and feedstock conditions in each of the several passes responsive to the analysis of effluent from the particular pass. This invention permits on-line decoking of an individual pass while maintaining optimum conditions in the remaining operational passes.

DETAILED DESCRIPTION OF THE INVENTION

The present invention is the result of the recognition that the cracking conditions for different parallel passes of a single furnace may vary considerably. Accordingly, significant differences are found in the effluents of the separate passes. If control of furnace conditions and feed is based on the analysis of the average effluent, which is the mixed effluent from the several parallel passes, the full advantages of optimization cannot be obtained.

Thus, this invention provides a process and apparatus for deriving optimum conditions for the operation of a hydrocarbon pyrolysis furnace with multiple passes. In particular, this invention is applicable to a pyrolysis furnace which is used for the conversion of a hydrocarbon feedstock in the presence of steam to produce a pyrolyzate containing ethylene, propylene, butadiene among other hydrocarbons and other reaction products.

Profitability of a pyrolysis process is dependent on optimization of pyrolysis conditions and cracking severity. An essential objective is to produce the most valuable effluent per pound of feed. Optimization is complicated considerably, for example, by the fact that hydrocarbon feeds vary and that for every feed there is a different optimum cracking severity to achieve optimum conversion and maximum profitability While it is generally true that higher furnace severity will give higher yields of valuable ethylene, higher severity will not necessarily give the desired optimization for several reasons. Essentially, exceeding the target conversion by using higher severity will tend to coke the coils reducing stream time between decoke cycles. There is also increased risk of doing damage to the coils during decoking operations. Moreover, the production of coke implies the loss of feed. Finally, excessive cracking increases fuel gas consumption and costs. Accordingly, the objectives of optimization are obtained by balancing a number of factors including obtaining a product of maximum value, and minimizing expense of feed, fuel, maintenance and operational expense.

The process broadly involves the analysis of the effluent from each of several parallel passes and the control of cracking conditions in that pass responsive to the analysis of the effluent for that pass.

The significance of the observed differences in cracking conditions of several passes of a multipass pyrolysis furnace is evident from the data in Tables 1 and 2. In Table 1, differences in ethane conversion from an EP (ethane propane) feed which is predominately ethane in various furnaces at different times are summarized. Similarly, Table 2 summarizes data for propane conversion from propane feeds. The present invention provides a means for improving optimization of furnace control to maximize profitability by taking into account the differences in actual and target severity in individual passes and using a feedback arrangement to effect target cracking severity in all passes of the furnace.

TABLE 1

| Furnace | Pass No. | EP FEED % C2 Conversion | Relative % Variance of % Conversion |
|---|---|---|---|
| D | 1 | 75.0 | −8.47 |
|   | 2 | 66.9 | 3.25 |
|   | 3 | 64.9 | 6.14 |
|   | 4 | 68.2 | 1.37 |
| F | 1 | 68.5 | 0.93 |
|   | 2 | 67.8 | 1.94 |
|   | 3 | 73.6 | −6.44 |
|   | 4 | 71.8 | −3.84 |
| C | 1 | 70.4 | −1.81 |
|   | 2 | 68.9 | 0.35 |
|   | 3 | 68.3 | 1.22 |
|   | 4 | 65.5 | 5.27 |
| C | 1 | 71.3 | −3.11 |
|   | 2 | 70.5 | −1.96 |
|   | 3 | 68.4 | 1.08 |
|   | 4 | 68.9 | 0.35 |
| F | 2 | 69.7 | −0.80 |
|   | 3* | 50.5 | 26.96 |
|   | 4 | 66.0 | 4.55 |
| Variation in Absolute % Conversion | | 10.10 | |
| Average Absolute % Conversion | | 69.14 | |
| Standard Deviation Absolute % Conversion | | 2.66 | |
| Standard Deviation Relative % Variance | | 3.85 | |

*Excluded from above

TABLE 2

| Furnace | Pass No. | PROPANE FEED % C3 Conversion | Relative % Variance of % Conversion |
|---|---|---|---|
| A | 1 | 85.6 | 4.01 |
|   | 2 | 88.4 | 0.87 |
|   | 3 | 92.8 | −4.07 |
|   | 4 | 84.5 | 5.24 |
| B | 1 | 94.3 | −5.75 |
|   | 3 | 80.1 | 10.17 |
|   | 4 | 88.2 | 1.09 |
| C | 2 | 91.5 | −2.61 |
|   | 3 | 84.4 | 5.35 |
|   | 4 | 87.6 | 1.76 |
| E | 1 | 88.0 | 1.31 |
|   | 2 | 97.2 | −9.00 |
|   | 3 | 94.4 | −5.86 |
|   | 4 | 91.4 | −2.50 |
| Variation in Absolute % Conversion | | 17.10 | |
| Average Absolute % Conversion | | 89.17 | |
| Standard Deviation Relative % Variation | | 4.70 | |

The process of this invention finds application with a variety of hydrocarbon feeds including gas feeds described in Table 3 and liquid feeds as described in Table 4. The furnace effluent can accordingly vary widely but typical constitution of effluent of the ethylene pyrolysis furnace is set forth in Table 5.

TABLE 3

| | GAS FURNACE FEEDS | | |
|---|---|---|---|
| COMPONENTS | ETHANE/ PROPANE | WT. % (RANGE) PROPANE | BUTANE |
| Methane | 0–2 | — | — |
| Ethane | 80–100 | 0–10 | — |
| Ethylene | 0–2 | — | — |
| Propane | 0–20 | 90–100 | 0–20 |
| Propylene | 0–0.2 | 0–2 | — |
| Butanes | | 0–1 | 0–70 |
| Butenes | 0–1 | 0–1 | 0–10 |
| C5+ | — | — | 0–3 |

TABLE 4

| COMPONENT | WT. % (RANGE) |
|---|---|
| C4's and lighter | 0–5 |
| Isopentane | 2–35 |
| N-pentane | 2–35 |
| C6's | 3–20 |
| C7's and heavier | 0–5 |

TABLE 5

| FURNACE EFFLUENT | |
|---|---|
| Hydrogen | 2.5–4.2 |
| Carbon Monoxide | 0.05–0.5 |
| Methane | 8.0–20.0 |
| Ethane | 2.0–30.0 |
| Ethylene | 20.0–55.0 |
| Acetylene | 0.5–2.5 |
| Propane | 0.5–10.0 |
| Propylene | 2.0–20.0 |
| Me-Acetylene - Propadiene | 0.5–2.5 |
| Butanes | 0.2–10.0 |
| Butenes | 0.2–5.0 |
| Butadiene | 1.0–5.0 |
| C5's | 0.5–5.0 |
| C6's | 0.0–1.0 |
| C7's | 0.1–1.0 |
| Benzene | 0.5–6.0 |
| Toluene | 0.5–3.0 |
| C8's | 0.0–5.0 |
| Residue | 0.0–2.0 |

DETAILED DESCRIPTION OF THE DRAWINGS

Figure 1:
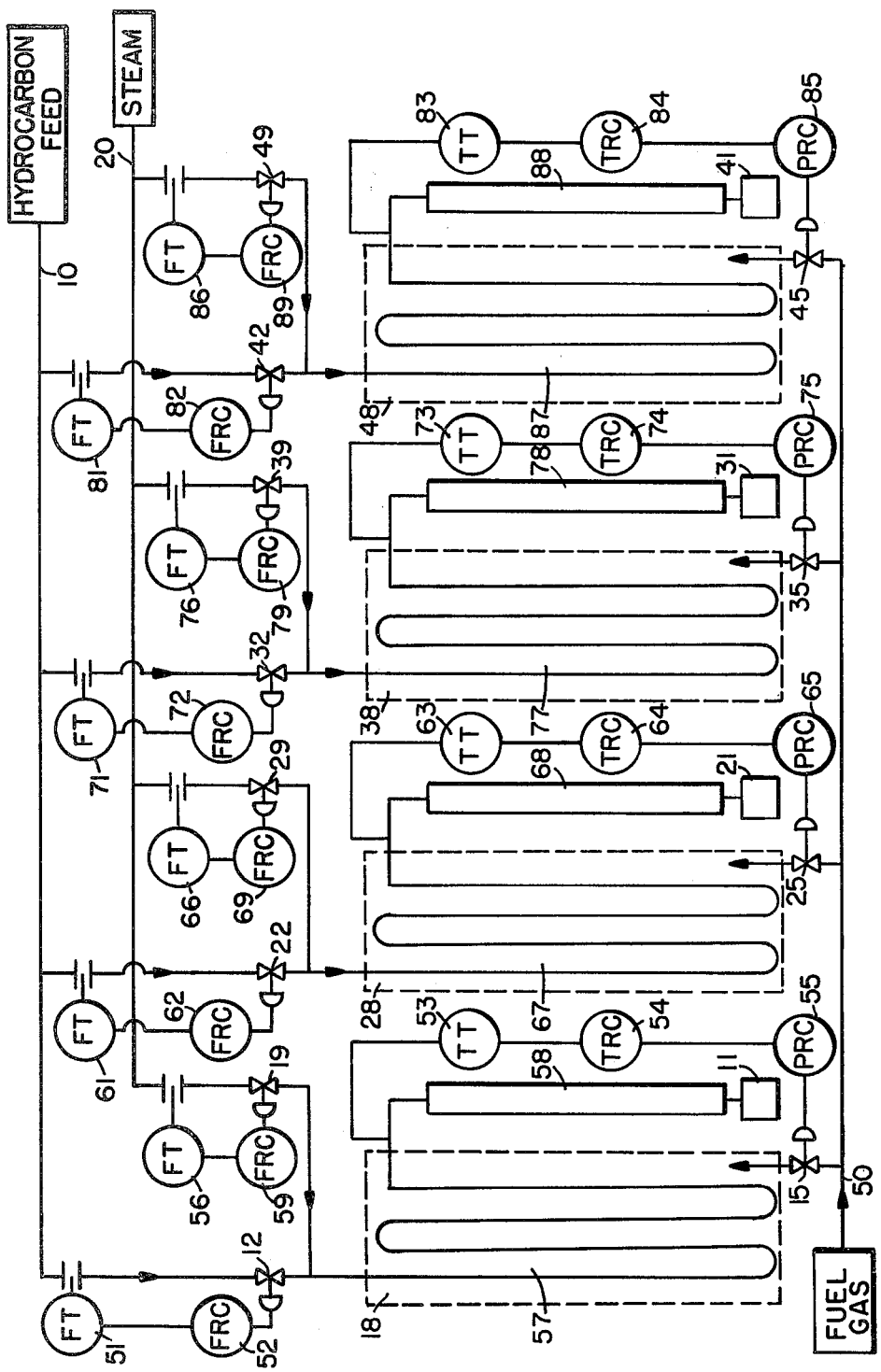
FIG. 1 is a schematic flow sheet of one embodiment of the invention showing a pyrolysis furnace having four passes with zone firing.

Referring now in detail to the drawings, FIG. 1 represents the control scheme for a pyrolysis furnace, with four parallel passes, consisting of four "W" shaped cracking coils 57, 67, 77 and 87 and zone firing with the zones represented by 18, 28, 38 and 48.

Hydrocarbon feed is supplied through line 10 to cracking coils in individual passes represented by 57, 67, 77 and 87. Hydrocarbon feed rate is monitored and controlled by flow transmitters 51, 61, 71 and 81 and flow recorder controllers 52, 62, 72 and 82 which adjust valves 12, 22, 32, and 42. Steam is provided through line 20 and its flow is monitored and controlled by steam flow transmitters 56, 66, 76 and 86 and steam flow recorder controllers 59, 69, 79 and 89 which adjust valves 19, 29, 39 and 49.

Downstream of the heat exchangers 58, 68, 78 and 88, effluent gas analyzers 11, 21, 31 and 41 analyze the product of pyrolysis. Coil outlet temperatures is monitored by temperature transmitters 53, 63, 73 and 83. Fuel gas is controlled in the separate passes by temperature recorder controllers 54, 64, 74, and 84 which reset pressure recorder controllers 55, 65, 75 and 85 to control the fuel gas pressure to the respective firing zones through adjustable valves 15, 25, 35 and 45. Fuel gas is supplied separately to each of the zones through fuel gas line 50.

It should be noted that "on-line" decoking of individual passes additionally contributes to the considerable variation in cracking conditions between the several passes and is another reason that actual cracking severities for individual pass effluents must be determined and controlled if most profitable and optimum furnace operation is to be realized.

Figure 2:
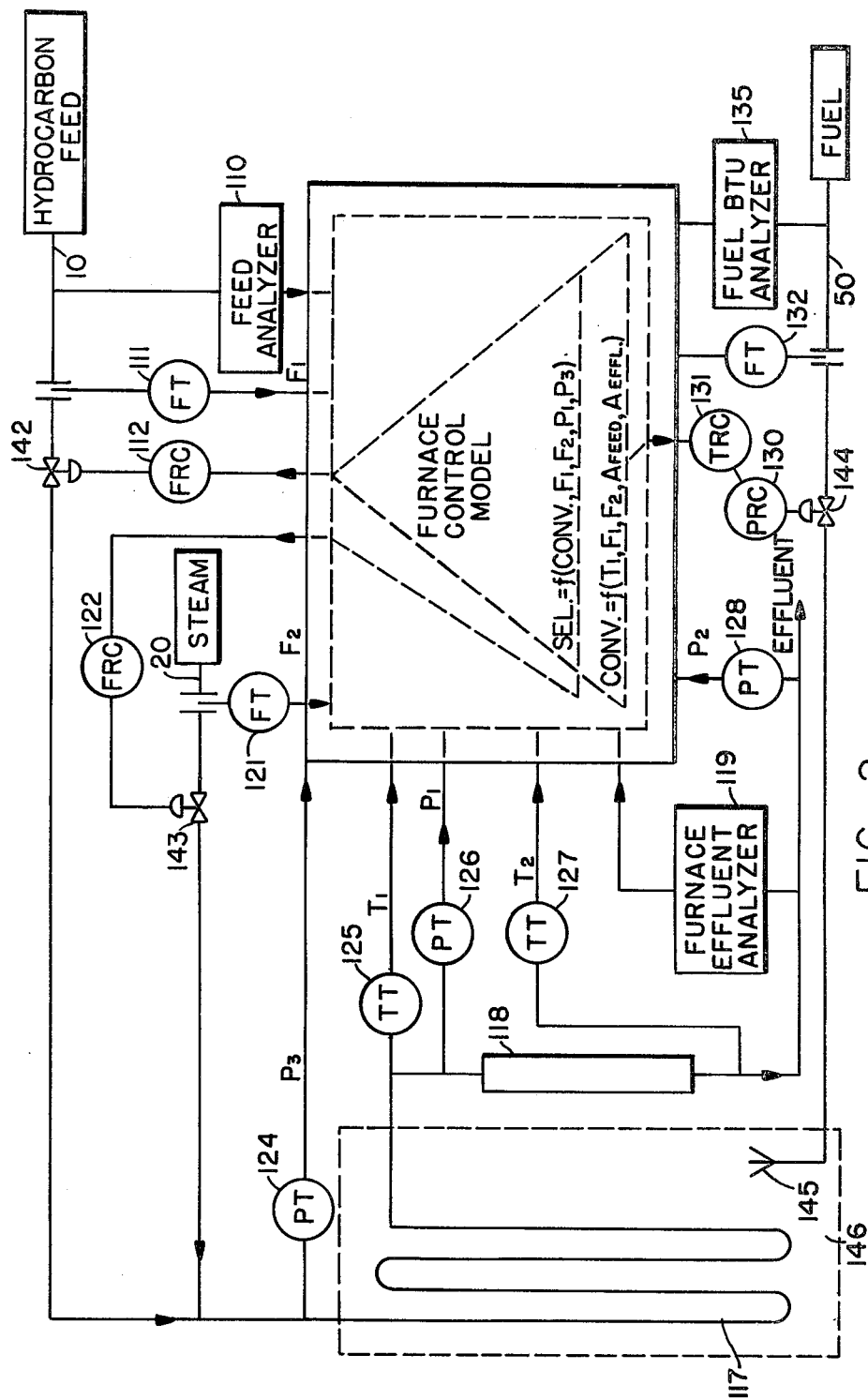
FIG. 2 is a schematic flow sheet showing the operation of a computer control and optimization system for a single pass of a multipass furnace.

In FIG. 3 a computer control and optimization scheme for a single pass of a multipass furnace such as described in FIG. 2 in which a suitably programmed process control computer is used. The furnace control model optimizes and controls the selectivity and conversion by the following equations.

$$\text{Selectivity} = f(\text{conversion}, F_1, F_2, P_1, P_3)$$
$$\text{Conversion} = f(T_1, F_1, F_2, A_{feed} \text{ and } A_{effl.})$$

$A_{feed}$ refers to the analysis of the hydrocarbon feed stream and $A_{effl.}$ refers to the analysis of the effluent.

The hydrocarbon feed supplied through line 10 is analyzed by the feed analyzer 110 and monitored and controlled by flow transmitter 111 and hydrocarbon flow recorder and controller 112 adjusting valve 142. Flow transmitter 111 transmits a signal $F_1$ and feed analyzer transmits a signal A feed to the computer. Cracking coil inlet pressure is measured by pressure transmitter 124 which generates the signal $P_3$. Steam flow is monitored and controlled by steam flow recorder and controller 122 through adjustable valve 143 and steam flow transmitter 121 which generates the signal $F_2$, steam being provided through the line 20. The cracking coil is represented by 117. Temperature of the effluent from the pass represented by the coil 117 is monitored by temperature transmitter 125 which generates the signal $T_1$. Pressure transmitter 126 generates the signal $P_1$ and a temperature transmitter 127 downstream generates the signal $T_2$. Downstream of the heat exchanger 118 furnace effluent is analyzed in the analyzer 119 generating the signal $A_{effl.}$. The pressure of the effluent after the first heat exchanger is monitored by the pressure transmitter 128 generating signal $P_2$. Fuel gas is supplied to the furnace in separate zones through fuel line 50. The fuel gas feed to the burner 145 for firing zone 146 is monitored by fuel flow transmitter 132 and is input to the control computer. Fuel flow is controlled by computer output which resets temperature recorder controller 132 set point. Temperature recorder controller 131 resets pressure recorder controller 130 to adjust fuel gas through adjustable valve 144 to maintain $T_1$ (cracking coil outlet temperature) at target as determined by the computer control model. Fuel BTU may be monitored with an analyzer 135.

Any suitable device can be used for the analyzers such as gas chromatographs.

I claim:

1. In a process for the pyrolysis of a feedstock in a pyrolysis furnace with multiple parallel passes which is controlled responsive to analysis of output, the improvement comprising analyzing the output at each of a plurality of said passes and individually controlling conditions in each of said plurality of passes responsive to the analysis of output of each respective pass.

2. The process of claim 1 in which the pyrolysis furnace is computer controlled.

3. The process of claim 1 in which includes control of fuel and pyrolysis temperature responsive to furnace output analysis.

4. The process of claim 1 which includes control of feedstock responsive to furnace output analysis.

5. The process of claim 1 in which a feedstock comprising $C_2$ and higher hydrocarbons and steam is pyrolyzed to a produce a product comprising ethylene.

6. The process of claim 1 in which the feedstock is analyzed and the measurement is used to control pyrolysis conditions.

7. An apparatus comprising, in combination, a pyrolysis furnace having a plurality of parallel passes, means for heating the plurality of parallel passes by combustion of a fuel whose flow is controllable, means for feeding one or more feedstock streams into said parallel passes and separate means for analysis of the effluent of each said parallel passes.

8. The apparatus of claim 7 which includes means for feedstock analysis.

9. The apparatus of claim 7 including means for controlling fuel, feedstock or both separately in each parallel pass in response to analysis of effluent from that pass.

10. The apparatus of claim 9 which includes means for feedstock analysis.

* * * * *

UNITED STATES PATENT AND TRADEMARK OFFICE
CERTIFICATE OF CORRECTION

PATENT NO. : 4,329,150

DATED : May 11, 1982

INVENTOR(S) : B. M. Drinkard

It is certified that error appears in the above—identified patent and that said Letters Patent is hereby corrected as shown below:

Column 4, line 3, "temperatures" should read -- temperature --.

Column 4, line 60, "132" should read -- 131 --.

Signed and Sealed this

Tenth Day of August 1982

[SEAL]

Attest:

GERALD J. MOSSINGHOFF

Attesting Officer     Commissioner of Patents and Trademarks